United States Patent
Parrish

(10) Patent No.: US 8,932,988 B2
(45) Date of Patent: Jan. 13, 2015

(54) CATIONIC SURFACTANT BASED ADJUVANT SYSTEMS FOR SOME HERBICIDES THAT INCREASE PH, HERBICIDE SOLUBILITY AND PERFORMANCE

(75) Inventor: Scott K. Parrish, Spokane, WA (US)

(73) Assignee: Agquam LLC, Spokane, WA (US)

( * ) Notice: Subject to any disclaimer, the term of this patent is extended or adjusted under 35 U.S.C. 154(b) by 1378 days.

(21) Appl. No.: 10/997,634

(22) Filed: Nov. 26, 2004

(65) Prior Publication Data

US 2009/0325805 A1    Dec. 31, 2009

(51) Int. Cl.

| | |
|---|---|
| A01N 47/36 | (2006.01) |
| A01N 25/00 | (2006.01) |
| A01N 65/00 | (2009.01) |
| A01N 43/60 | (2006.01) |
| A01N 43/54 | (2006.01) |
| A01N 25/30 | (2006.01) |

(52) U.S. Cl.
CPC ..................................... *A01N 25/30* (2013.01)
USPC ........ 504/211; 504/116.1; 504/189; 504/210; 504/212; 504/214; 504/215; 504/216; 504/235; 504/239; 504/358

(58) Field of Classification Search
USPC ...................... 504/211, 116.1, 189, 210, 212, 504/214–216, 235, 239, 358
See application file for complete search history.

(56) References Cited

U.S. PATENT DOCUMENTS

| | | | |
|---|---|---|---|
| 3,879,188 A | | 4/1975 | Fritz et al. |
| 4,119,399 A | * | 10/1978 | Feinland et al. .................. 8/412 |
| 4,331,572 A | * | 5/1982 | Tomasi et al. ................. 524/238 |
| 4,840,660 A | | 6/1989 | Kowite |
| 5,078,782 A | | 1/1992 | Nielsen et al. |
| 5,116,401 A | | 5/1992 | Young |
| 5,302,579 A | | 4/1994 | Young |
| 5,389,598 A | | 2/1995 | Berk et al. |
| 5,541,149 A | | 7/1996 | Atwater et al. |
| 5,658,855 A | | 8/1997 | Nalewaja et al. |
| 5,683,958 A | | 11/1997 | Berger et al. |
| 5,877,112 A | | 3/1999 | Roberts et al. |
| 6,180,566 B1 | | 1/2001 | Nielsen et al. |
| 6,369,001 B1 | | 4/2002 | Jimoh |
| 6,541,424 B2 | | 4/2003 | Roberts et al. |
| 6,803,345 B2 | | 10/2004 | Herold et al. |
| 6,906,004 B2 | | 6/2005 | Parrish et al. |
| 7,094,735 B2 | | 8/2006 | Herold et al. |
| 8,034,744 B2 | | 10/2011 | Parrish |
| 2002/0107149 A1 | | 8/2002 | Volgas et al. |
| 2002/0160916 A1 | | 10/2002 | Volgas et al. |
| 2003/0104947 A1 | * | 6/2003 | Woznica et al. ............... 504/363 |
| 2003/0125211 A1 | * | 7/2003 | Woznica et al. ............... 504/363 |
| 2003/0144147 A1 | | 7/2003 | Herold et al. |
| 2003/0148889 A1 | | 8/2003 | Herold et al. |
| 2003/0153461 A1 | | 8/2003 | Parrish et al. |
| 2003/0153462 A1 | | 8/2003 | Herold et al. |
| 2004/0097372 A1 | * | 5/2004 | Abraham et al. ............. 504/127 |
| 2004/0127364 A1 | | 7/2004 | Herold et al. |
| 2004/0167032 A1 | | 8/2004 | Volgas et al. |
| 2005/0170967 A1 | | 8/2005 | Parrish et al. |
| 2006/0205601 A1 | | 9/2006 | Herold et al. |
| 2006/0270557 A1 | | 11/2006 | Volgas et al. |
| 2007/0037707 A1 | | 2/2007 | Volgas et al. |

FOREIGN PATENT DOCUMENTS

| | | |
|---|---|---|
| CN | 1252940 | 5/2000 |
| CN | 1302545 | 7/2001 |

OTHER PUBLICATIONS

Sure Up (The SU SUrfactant) product guide, revised on Mar. 6, 2004.*
Green, J. M. (Weed Technology: 1996, vol. 10, p. 508-511).*
Green et al. (1993) Weed Technology 7:633-640, Surfactant Structure and concentration Strongy Affect Rimsulfuron Activity.
Bohn et al. (1985) "Salt-Affected Soil, 8.6 Reclamation" Soil Chemistry, 2nd Ed, Wiley Interscience pp. 241-243.
Brown et al. (2003) "Cotton Defliation", Harvest Aid Suggestions.
CABA abstract 80:49077 (Nov. 1994).
Cox Glyphosate Factsheet, Journal of Pesticide Reform 2000, 108(3) part 1 and part 2.
Derwent Abstract 1997-133542; abstracting CN 1038382 C (1998).
Ethephon Publication, EPA Pesticide Fact Sheet (online) Sep. 1988. Retrieved from the internet on Nov. 19, 2008:<URL: http://pmep.cce.cornell.edu/profiles/herb-growthreg/dalapon-ethephon/etheph_prf_0988.html>.
Farm Chemicals Handbook '98, Meister Publishing Co., Willoughby, Ohio, 1998, p. C164.
Greenhouse Product News (Feb. 1999) "Water Chemistry as it Applies to pH and Alkalinity".
Gwathmey and Hayes (1997) "Harvest-Aid Interactions Under Different Temperature Regimes in Field-Grown Cotton", Journal of Cotton Science 1:1-9.
HCAPLUS abstract 2000:843249 (Dec. 2000).
Hartzler (2001) "Role of AMS with Glyphosate Products", R. Extension Bulletin, Iowa State University.

(Continued)

*Primary Examiner* — Mina Haghighatian
*Assistant Examiner* — Helen Chui
(74) *Attorney, Agent, or Firm* — Swanson & Bratschun, L.L.C.

(57) ABSTRACT

A method for increasing the performance of sulfonylurea and sulfonamide herbicides by using blends of cat-ionic surfactants and basic pH adjustors as adjuvants.

6 Claims, No Drawings

(56) References Cited

OTHER PUBLICATIONS

Imidacloprid Publication, NYState Dept. of Environmental Conservation (online) Mar. 1995. Retrieved from the internet on Nov. 19, 2008:<URL:http://pmep.cce.cornell.edu/profiles/insect-mite/fenitrothion-methylpara/imidacloprid/imidac_let_0395.html>.

Nalewaja and Matysiak (1993) "Influence of Diammonium Sulfate and Other Salts on Glyphosate Phytotoxicity", Pesticide Sci. 38:77-84.

Office Action mailed Apr. 19, 2006 with respect to U.S. Appl. No. 10/728,419.

Office Action mailed Oct. 16, 2006 with respect to U.S. Appl. No. 10/728,419.

Office Action Final mailed Apr. 19, 2007 with respect to U.S. Appl. No. 10/728,419.

Office Action mailed Feb. 4, 2008 with respect to U.S. Appl. No. 10/728,419.

Office Action Final mailed Nov. 24, 2008 with respect to U.S. Appl. No. 10/728,419.

Office Action mailed Aug. 10, 2009 with respect to U.S. Appl. No. 10/728,419.

Office Action mailed May 16, 2006 with respect to U.S. Appl. No. 10/853,781.

Office Action mailed Mar. 6, 2007 with respect to U.S. Appl. No. 10/853,781.

Office Action Final mailed Jul. 27, 2007 with respect to U.S. Appl. No. 10/853,781.

Office Action mailed Apr. 15, 2008 with respect to U.S. Appl. No. 10/853,781.

Office Action Final mailed Jan. 21, 2009 with respect to U.S. Appl. No. 10/853,781.

Office Action mailed Sep. 24, 2009 with respect to U.S. Appl. No. 10/853,781.

Petroff R. Water Effects on Pesticide Performance Apr. 12, 2003 (online) Retrieved from the internet <URL: http://web.archive.org/web/20030412083321/http://www.co.fergus.mt.us/weed/Water+Effects+on+Pesticide+Efficacy.html.>.

Petroff (2000) "Water Quality and Pesticide Performance", Pesticide Education Specialist, Montana State University Extension Service.

Reed (1996) "Water Quality Management for Greenhouse Production", Ball Publishing, Batavia, IL, ISBN: 1-883052-12-2.

The Agrochemicals Handbook, Unwin Brothers Ltd., Old Working (Surrey), United Kingdom, pp. A179, A180, the entry for "ethephon", Oct. 1983.

The American Heritage Dictionary 1982 "include" 3 pages.

Thelen et al. (1995) "The Basis for the Hard-Water Antagonism of Glyphosate Activity", Weed Science 43(4):541-548.

WPIDS Abstract 1986-007470; Abstracting DD 227034 A (1985).

Wright and Brecke (2006) "Cotton Defoliation and Harvest Guide", University of Florida, Institute of Food and Agricultural Sciences.

Carlson and Burnside (1984) "Comparative Phytotoxicity of Glyphosate, SC-0224, SC-0545, and HOE-00661", Weed Science 32:841-844.

Nalewaja and Matysiak (1991) "Salt Antagonism of Glyphosate", Weed Science 39:622-628.

\* cited by examiner

CATIONIC SURFACTANT BASED ADJUVANT SYSTEMS FOR SOME HERBICIDES THAT INCREASE PH, HERBICIDE SOLUBILITY AND PERFORMANCE

CROSS-REFERENCE TO RELATED APPLICATIONS

1) Nalewaja; John D Aug. 19, 1997 U.S. Pat. No. 5,658,855
2) M. Green et al., "Surfactant Structure and Concentration Strongly Affect Rimsulfuron Activity", Weed Technology, 1993, vol. 7:633-640.
3) Woznica, Zenon J.; et al. Jul. 3, 2003 Patent Application Number 20030125211.
4) Woznica, Zenon J.; et al. Jun. 5, 2003 Patent Application Number 20030104947

BACKGROUND OF THE INVENTION

It is known that increasing the pH of the spray solution for sulfonylurea herbicides increases the performance of these herbicides[1]. This can be achieved by using a number of pH adjustors which can also be applied with fertilizers or adjuvant blends. It is thought that the effect is due to an increase in solubility of these types of herbicides as the pH increases (WSSA *Herbicide* Handbook—7th Edition, 1994). This invention pertains to the use of a pH adjustor in a blend of cat-ionic surfactants. It was discovered that Sulfosulfuron, a sulfonylurea herbicides, performed better when the pH adjustor was combined with a cat-ionic surfactant (amine) rather than an oil or a blend of non-Ionic surfactants as taught by Nalewaja et. al.

SUMMARY OF THE INVENTION

The present invention relates to adjuvant compositions for use in the spray carrier of post emergence herbicides applied as an aqueous spray solution to crops infested with undesired weeds to control the infesting weeds. Broadly, the adjuvant compositions of the invention comprise an amine or ammonia compounds for adjusting the pH to the alkaline range of 9-10.5 and a cat-ionic surface active agent with a high Hydrophilic-Lipophilic balance (HLB), which functions as a spreader or sticker and penetrant for use with postemergence sulfonylurea and sulfonamide herbicides when applied in a aqueous spray composition.

Normally the adjuvant is applied as 0.5% v/v (volume to volume) of the aqueous spray solution. In other words, the present invention is diluted with water (99.5%) to which is added the desired herbicide, normally sulfosulfuron. However, increases in activity have been seen with other sulfonylurea or sulfonamide herbicides. Sulfonylurea herbicides contemplated herein include sulfosulfuron, triasulfuron, mesosulfuron-methyl, chlorsulfuron, halosulfuron, metsulfuron, thifensulfuron, tribenuron, bensulfuron, primisulfuron, and nicosulfuron. Sulfonamide herbicides contemplated herein include propoxycarbazone-sodium and cloransulammethyl.

DETAILED DESCRIPTION OF THE INVENTION

This invention pertains to the unexpected increase in activity seen when sulfosulfuron was applied with a cat-ionic surfactant plus a pH adjustor that increased the pH to a pH of 9-10.5 (Table 1). As opposed to the increase in activity that was predicted to happen when applied with an oil based or non-ionic surfactant with a pH adjustor as taught by Nalewaja et. al.

This effect has been seen with both wild oat (*Avena fatua*) Table 1 and downy brome (*Bromus tectorum*) Table 2. The increase in activity has been seen with different formulation of tallow amine cat-ionic surfactant and a pH increasing additive (Table 3).

TABLE 1

The Efficacy (Percent Control) of Sulfosulfuron as Affected by Differing Spray Adjuvants Applied to Wild Oats. Use Rate of Sulfosulfuron 0.66 oz/Acre. Days After Treatment (DAT).

| Herbicide | Adjuvant | Wild Oat % Control 14 DAT | Wild Oat % Control 28 DAT |
|---|---|---|---|
| Sulfosulfuron | Quad 7* | 48% | 62% |
| Sulfosulfuron | AQ118** | 75% | 98% |

*Quad 7: Crop Oil plus nitrogen fertilizer to increase pH and herbicidal activity.
**AQ118: Tallow Amine (cat-ionic surfactant) plus Aqua Ammonia.

TABLE 2

The Efficacy (Percent Control) of Sulfosulfuron and Propoxycarbazone-sodium Applied with Differing Spray Adjuvants to Downy Brome (*Bromus tectorum*). Ratings made 21 and 68 Days After Treatment (DAT

| Herbicide | Adjuvant | Downy Brome % Control 21 DAT | Downy Brome % Control 68 DAT |
|---|---|---|---|
| Sulfosulfuron | *AQ117 | 78% | 97% |
| Sulfosulfuron | **R-11 | 52% | 62% |
| Propoxycarbazone | AQ117 | 73% | 90% |
| Propoxycarbazone | R-11 | 52% | 67% |

*AQ117: Tallow Amine (cat-ionic surfactant) plus Aqua Ammonia.
**R-11: Non-Ionic surfactant

TABLE 3

The Efficacy (Percent Control) of Sulfosulfuron Applied with Differing Spray Adjuvants to Downy Brome (*Bromus tectorum*). Ratings made 17 and 68 Days After Treatment (DAT

| Herbicide | Adjuvant | Downy Brome % Control 17 DAT | Downy Brome % Control 87 DAT |
|---|---|---|---|
| Sulfosulfuron | *AQ103 | 30% | 92% |
| Sulfosulfuron | **AQ104 | 30% | 90% |
| Sulfosulfuron | ***R-11 | 5% | 77% |

*AQ103: Tallow Amine (cat-ionic surfactant) plus Aqua Ammonia.
**AQ104: Tallow Amine (cat-ionic surfactant) plus Aqua Ammonia.
***R-11: Non-Ionic surfactant The constituents of the proposed mixture are normally made up of cat-ionic amine surfactant and a pH adjustor that increases the pH. The cat-ionic surfactant Alkyl Dimethylamines, Alkyl Amidopropylamines, Alkyl Imidazoline, Derivatives Quaternised, Amine Ethoxylates, Quaternary Ammonium Compounds. In certain embodiments, the alkaline pH adjustor includes, but is not limited to: ammonium hydroxide, potassium hydroxide, sodium hydroxide monoethanolamine, diethanolamine, triethanolamine, and mixtures thereof. In certain embodiments, the cationic surfactant includes, but is not limited to: tallow amine, tallow diamine, coco amines, ether amines, and mixtures thereof. In certain embodiments, the adjuvant blend comprises vegetable oils and mixtures thereof. In certain embodiments, the adjuvant blend comprises modified vegetable oils selected from the group consisting of methylated, ethylated and butylated seed oils and mixtures thereof. In certain embodiments, the herbicide includes but is not limited to sulfonylurea herbicides such as sulfosulfuron, triasulfuron, mesosulfuron-methyl, chlorsulfuron, halosulfuron, metsulfuron, thifensulfuron, tribenuron, bensulfuron, primisulfuron, and nicosulfuron. In certain embodiments, the herbicide includes but is not limited to sulfonamide herbicides such as propoxycarbazone-sodium, and cloransulam-methyl. In certain embodiments, the mixture may contain a linear alcohol ethyoxylate.

I claim:

1. An aqueous herbicidal spray composition consisting of:
    an adjuvant blend consisting of a cationic surfactant and a basic pH adjustor in an amount effective for providing an alkaline pH of above 9 to about 10.5 when formulated in the aqueous spray composition; and
    an effective amount of a sulfonylurea or sulfonamide herbicide.

2. The composition according to claim 1 where the basic pH adjustor is selected from the group consisting of ammonium hydroxide, potassium hydroxide, sodium hydroxide monoethanolamine, diethanolamine, triethanolamine, and mixtures thereof.

3. The composition according to claim 1 where the cationic surfactant is selected from the group consisting of tallow amine, tallow diamine, coco amines, ether amines, and mixtures thereof.

4. The composition of claim 1 wherein said herbicide is a sulfonylurea.

5. The composition of claim 1 wherein said herbicide is selected from the group consisting of sulfosulfuron, mesosulfuron-methyl, nicosulfuron, and propoxycarbazone.

6. An aqueous herbicidal spray composition consisting of:
    an adjuvant blend consisting of a tallow amine and ammonium hydroxide, wherein the ammonium hydroxide is present in an amount effective for providing an alkaline pH of above 9 to about 10.5 when formulated in the aqueous spray composition; and
    an effective amount of a sulfonylurea or sulfonamide herbicide.

* * * * *